US012109439B2

(12) United States Patent
Bar-David et al.

(10) Patent No.: US 12,109,439 B2
(45) Date of Patent: Oct. 8, 2024

(54) METHOD OF ESTIMATING DOSIMETRIC CHARACTERISTICS X-RAY CONVERGENT IRRADIATOR TO OBJECT TO BE IRRADIATED

(71) Applicant: Convergent R.N.R Ltd., Tirat Carmel (IL)

(72) Inventors: Aharon Bar-David, Nesher (IL); Michael Kleckner, Ramat-Yishai (IL); Shirly Borukhin, Atlit (IL); Zeev Harel, Kfar Saba (IL)

(73) Assignee: Convergent R.N.R Ltd., Tirat Carmel (IL)

( * ) Notice: Subject to any disclaimer, the term of this patent is extended or adjusted under 35 U.S.C. 154(b) by 920 days.

(21) Appl. No.: 17/166,064

(22) Filed: Feb. 3, 2021

(65) Prior Publication Data

US 2021/0178192 A1 Jun. 17, 2021

Related U.S. Application Data

(63) Continuation-in-part of application No. 16/258,612, filed on Jan. 27, 2019, now abandoned, which is a
(Continued)

(51) Int. Cl.
*A61N 5/10* (2006.01)

(52) U.S. Cl.
CPC ......... *A61N 5/1075* (2013.01); *A61N 5/1065* (2013.01); *A61N 2005/1076* (2013.01); *A61N 2005/1085* (2013.01)

(58) Field of Classification Search
CPC ............... A61N 5/1075; A61N 5/1065; A61N 2005/1076; A61N 2005/1085
See application file for complete search history.

(56) References Cited

U.S. PATENT DOCUMENTS 6,200,255 B1   3/2001 Yu
6,411,675 B1   6/2002 Llacer
(Continued)

FOREIGN PATENT DOCUMENTS

WO   2011091014 A2   7/2011
WO   2012023141 A1   2/2012
(Continued)

OTHER PUBLICATIONS

PCT International Search Report for International Application No. PCT/IL2014/051065, mailed Apr. 26, 2015, 11pp.
(Continued)

*Primary Examiner* — Thaddeus B Cox
*Assistant Examiner* — Joshua Daryl D Lannu
(74) *Attorney, Agent, or Firm* — The Roy Gross Law Firm, LLC; Roy Gross

(57) ABSTRACT

A method of a radiotherapy or radiosurgery treatment comprises steps of: (a) providing a converging x-ray beam source configured for emitting a converging X-ray beam propagating along an axis thereof; (b) emitting the converging x-ray beam towards a volume of treatment (VOT) having a length along the axis of the converging X-ray beam ranging between 2 mm and 5 cm within a patient's body such that a waist portion is within the VOT; (c) propagating the beam through tissues previously located relative to the VOT (PO); the VOT per se and tissues distally located to the VOT (DO). The converging X-ray beam characterized by a convergent angle ranging between 2 and 30 degrees providing 80% to 100% of a maximum dose is received by the VOT and less than 60% of the maximum dose is received by the PO and the DO.

8 Claims, 5 Drawing Sheets

Related U.S. Application Data continuation-in-part of application No. 15/102,713, filed as application No. PCT/IL2014/051065 on Dec. 7, 2014, now abandoned.

(60) Provisional application No. 61/913,937, filed on Dec. 10, 2013.

(56) References Cited

U.S. PATENT DOCUMENTS

| | | |
|---|---|---|
| 8,222,616 B2 | 7/2012 | Lu et al. |
| 2003/0212325 A1 | 11/2003 | Cotrutz et al. |
| 2004/0116767 A1 | 6/2004 | Lebovic et al. |
| 2005/0111621 A1 | 5/2005 | Riker et al. |
| 2005/0207531 A1 | 9/2005 | Dempsey et al. |
| 2007/0034812 A1 | 2/2007 | Ma et al. |
| 2007/0127623 A1 | 6/2007 | Goldman et al. |
| 2007/0195930 A1 | 8/2007 | Kapatoes et al. |
| 2009/0110145 A1 | 4/2009 | Lu et al. |
| 2011/0091014 A1 * | 4/2011 | Siljamaki ............ A61N 5/1031 378/65 |
| 2012/0020460 A1 | 1/2012 | Witten et al. |
| 2013/0197878 A1 | 8/2013 | Fiege et al. |
| 2013/0324784 A1 | 12/2013 | Fredriksson |
| 2014/0107392 A1 | 4/2014 | Gurvich et al. |
| 2018/0133513 A1 | 5/2018 | Bar-David et al. |

FOREIGN PATENT DOCUMENTS

| | | | |
|---|---|---|---|
| WO | WO-2013121418 A1 * | 8/2013 | ............... A61B 6/06 |
| WO | 2015087319 A1 | 6/2015 | |

OTHER PUBLICATIONS

PCT Written Opinion for International Application No. PCT/IL2014/051065, mailed Apr. 26, 2015, 9pp.

PCT International Preliminary Report on Patentability for International Application No. PCT/IL2014/051065, completed May 10, 2016, 21pp.

Radiation Oncology Physics: A Handbook for Teachers and Students. (2005) E.B. Podgorsak (Technical Ed.) International Atomic Energy Agency, Vienna.

Bartkoski, D.A., Bar-David, A., Kleckner, M. et al. Analysis of a novel X-ray lens for converging beam radiotherapy. Sci Rep 11, 19180 (2021). https://doi.org/10.1038/s41598-021-98888-8.

* cited by examiner

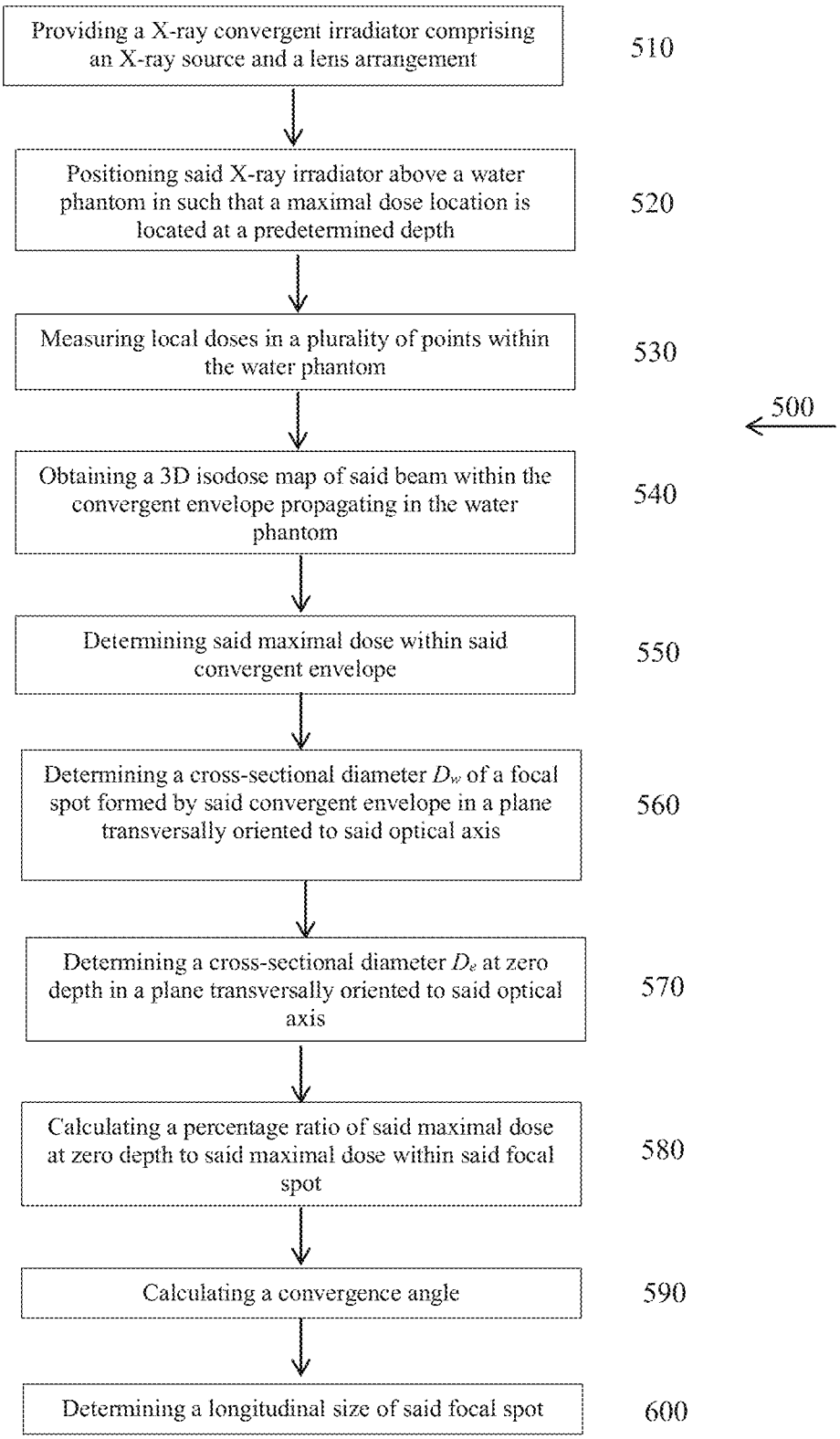

METHOD OF ESTIMATING DOSIMETRIC CHARACTERISTICS X-RAY CONVERGENT IRRADIATOR TO OBJECT TO BE IRRADIATED

CROSS REFERENCE TO RELATED APPLICATIONS

This application is Continuation-in-Part of U.S. patent application Ser. No. 16/258,612, filed on Jan. 27, 2019, which is a Continuation-in-Part of U.S. patent application Ser. No. 15/102,713, filed on Jun. 8, 2016 which is a national phase filing of International (PCT) Pat. Appl. No. PCT/IL2014/051065, filed on Dec. 7, 2014, and claims priority from U.S. Provisional Pat. Appl. No. 61/913,937, filed on Dec. 10, 2013. All of these earlier applications are incorporated by reference in their entirety.

FIELD OF THE INVENTION

The current invention pertains to radiotherapy and radiosurgery and, more particularly, to X-ray sources generating a convergent beam.

BACKGROUND OF THE INVENTION

Radiation therapy (radiotherapy) uses high-energy ionizing radiation to control tumors, kill cancer cells and prevent their recurrence. About 60% of cancer cases require radiation therapy while the most common types of cancer treated that way are prostate, skin, head and neck, throat, larynx, breast, brain, colon-rectal, lung, bone, leukemia, ovarian, and uterine. In some cases, radiotherapy is combined with chemotherapy and/or surgical removal of the cancerous tumor. In any case a radiotherapy or radiosurgery treatment plan is made.

The goal of a treatment plan is to target the radiation to the tumor with minimal effect on the surrounding healthy tissue. The plan is contemplated according to simulations on the patient's inner body imaging data, which are used to plan the geometric, radiological, and dosimetric aspects of the therapy using radiation transport simulations and optimization. Plans are often assessed with the aid of dose-volume histograms (DVH), allowing the clinician to evaluate the uniformity of the dose to the diseased tissue (tumor) and sparing of healthy structures.

In all inner-body radiotherapy or radiosurgery treatment s, radiation passes through healthy tissue on its way to and from the volume of the patient's body that is under treatment causing various adverse effects. The main reported adverse effects are fatigue and skin irritation. Additional short-term adverse effects are: nausea and vomiting, damage to the epithelial diseased tissue, mouth and throat sores, intestinal discomfort, swelling, infertility and various other adverse effects of different amount of severity. Long-term effects are: fibrosis, dryness, lymphedema, secondary cancer, heart disease, cognitive decline and radiation proctitis.

In order to reduce damage to healthy tissue in radiation therapy and to prevent adverse effects caused by it, different delivery systems of radiation that reduce their exposure to healthy tissue were suggested. For example, brachytherapy places a radiation source in or next to the volume requiring therapy. For example, US2004116767 patent application suggests a device for providing radiation to treat breast cancer, and U.S. Pat. No. 6,200,255 patent offers a device for delivering radiotherapy to the prostate gland. The major disadvantage of brachytherapy is that it requires an invasive procedure, which many patients, already very ill, will not be able to tolerate.

Today's radiotherapy and radiosurgery treatments are done using linear accelerators (LINAC). The main disadvantages of LINACs include: Non-converging (even diverging) beams, which causes the need to scan the body from many directions: use of high energy photons in the range of a few MeV up to about 25 MeV, which causes the beam to be only little attenuated after it passes the volume of treatment (VOT): high cost of the machine and its accessories and more.

There thus remains a long felt need for a standard of care protocol for radiotherapy or radiosurgery treatments that will improve the quality of the treatment, reduce substantially the number of sessions needed as well as reduce the amount and severity of adverse effects without requiring an invasive procedure. It is important to reduce long-term effects, but nonetheless, it is important to reduce the short-term effects as well. The latter, though not life threatening, add to the stress and anxiety and may interfere with the heeling progression.

Converging beam are suggested in some publications such as for example in U.S. Pat. No. 9,008,271 and others, but none of them characterizes the converging properties used for the applicability of the generated convergent beams to specific problem in terms of minimization of adverse effects of the irradiation while maintaining the accuracy of killing a tumor. Thus, there is a long-felt and unmet need for providing a method of estimating dosimetric characteristics of an x-ray convergent irradiator

SUMMARY OF THE INVENTION

It is hence one object of the invention to disclose a method of estimating dosimetric characteristics provided by an x-ray convergent irradiator. The aforesaid method comprises steps of: (a) providing said X-ray convergent irradiator comprising an X-ray source and a lens arrangement configured for forming an X-ray beam with a convergent envelope; said X-ray beam having an optical axis thereof; (b) positioning said X-ray irradiator above a water phantom in such that a maximal dose location is located at a predetermined depth; (c) measuring local doses in a plurality of points within said water phantom; (d) obtaining a 3D isodose map within said convergent envelope propagating in said water phantom; (e) determining said maximal dose within said convergent envelope; (f) on the basis of said 3D isodose map, determining a cross-sectional diameter $D_w$ of a focal spot formed by said convergent envelope in a plane transversally oriented to said optical axis; (g) on the basis of said 3D isodose map, determining a cross-sectional diameter $D_e$ at zero depth in a plane transversally oriented to said optical axis; (h) calculating a percentage ratio of said maximal dose at zero depth to said maximal dose within said focal spot $$R_{em} \equiv \frac{\text{Dose at depth 0}}{\text{Maximum dose at the focus}}; (i)$$

calculating a convergence angle given as arctan $$\alpha = \arctan\left(\frac{D_e - D_w}{2L}\right),$$

where $D_e$ and $D_w$ are cross-sectional diameters of said convergent envelope at said zero depth and said focal spot; and (j) determining a longitudinal size of said focal spot according to a predetermined criterion.

Another object of the invention is to disclose the predetermined depth which is 8 cm.

Another object of the invention is to disclose the predetermined criterion which is a region where 80%-100% of said maximal dose is received.

Another object of the invention is to disclose the water phantom which is a tissue equivalent in terms of the dosimetric characteristics of both water and human tissue Another object of the invention is to disclose a method of irradiating a target by an X-ray convergent irradiator with an estimated dose. The aforesaid method comprises steps of: (a) estimating dosimetric characteristics provided by said x-ray convergent irradiator, (b) on the basis of obtained percentage ratio, convergence angle and longitudinal size of focal spot, estimating the dose to be provided to said target; and (c) irradiating said target with said estimated dose.

Another object of the invention is to disclose a method of radio treatment a patient by an X-ray convergent irradiator with an estimated dose. The aforesaid method comprises steps of: (a) estimating dosimetric characteristics provided by said x-ray convergent irradiator, (b) on the basis of obtained percentage ratio, convergence angle and longitudinal size of focal spot, estimating the dose to be provided to said target; and (c) irradiating said target with said estimated dose.

BRIEF DESCRIPTION OF THE FIGURES

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not necessarily obscured. In the accompanying drawing:

FIG. 4 is a longitudinal cross-sectional view of a converging beam; and.

FIG. 5 is a flowchart of a method of estimating dosimetric characteristics provided by an x-ray convergent irradiator.

DETAILED DESCRIPTION OF THE PREFERRED EMBODIMENTS

Figure 1:
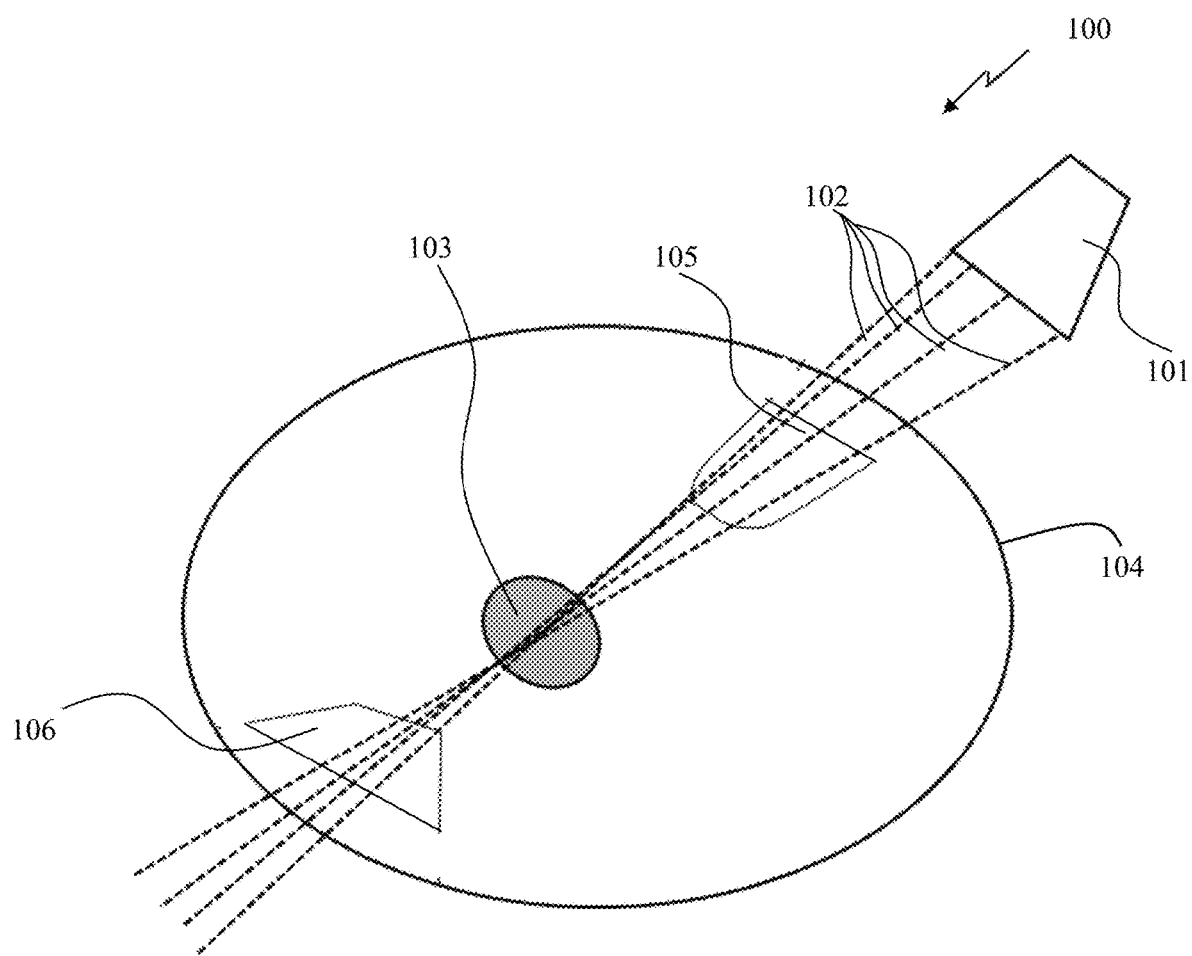
FIG. 1 schematically illustrates a radiotherapy or radiosurgery treatment with a converging x-ray beam source (100)

The following description is provided, alongside all chapters of the present invention, so as to enable any person skilled in the art to make use of the invention and set forth the best modes contemplated by the inventor of carrying out this invention. Various modifications, however, will remain apparent to those skilled in the art, since the generic principles of the present invention is defined to specifically provide a method of estimating dosimetric characteristics provided by an x-ray convergent irradiator.

The term "single shot" refers to a single shot in a single direction.

The term "radiotherapy" refers hereinafter to the medical use of ionizing radiation, generally as part of cancer treatment to control or kill malignant cells. It may also be used as part of adjuvant therapy, to prevent tumor recurrence after surgery that removes a primary malignant tumor. Radiation therapy may be synergistic with chemotherapy, and may be used before, during, and after chemotherapy in susceptible cancers. According one embodiment, radiotherapy relates to a mode of treatment wherein the therapeutic dose can be administered in more than one fraction, usually in a number of fractions, for example in more than 10 fractions.

The term "adverse effects" refers hereinafter to a harmful and undesired effect resulting from the radiotherapy or radiosurgery treatment.

The term "convergent x-ray beam" refers to a beam whose rays start from separate spread locations and converging to a common location—the focal location—at the focal distance. It can be a point—focal point, or small cross section area at the focal plane, the waist of the converging beam. Thus, the average radiation flux cross section area density is increasing along the longitudinal axis until reaching a maximum related to the focal location. Beyond the focal distance the rays diverge. The convergence of the x-ray beam improves the quality of the treatment, reduces substantially the number of sessions needed as well as reduces the amount and severity of adverse effects without requiring an invasive procedure.

The term "bodily cavity" refers herein after to a natural hollow or sinus within the body. More specifically the term refers to the oral cavity, anal cavity, vagina, nasal cavity, ear cavity, eye socket, etc.

The term "internal organ" refers herein after to an organ that is situated inside the body. More specifically, the term relates to the heart, kidney, lungs, liver, womb, bone and any other organ within the body.

The term "radiosurgery" refers hereinafter to a regime of treatment with fewer sessions than the number of treatments used in radiotherapy, of a much higher dose in each session.

The term "volume of treatment (VOT)" refers hereinafter to the volume of the treated target. This term usually refers to a cancerous tumor.

The term "preceding organ (PO)" refers hereinafter to an organ that precedes the VOT in the trajectory of the x-ray beam. More generally, the term refers, for example, to skin, brain, liver, kidney, heart, lungs, etc.

The term "distal organ (DO)" refers hereinafter to an organ that follows the VOT in the trajectory of the x-ray beam. More generally, the term refers, for example, to skin, brain, liver, kidney, heart, lungs, etc.

The term "focal point" refers hereinafter to the point at which the converging x-ray beams meet.

The term "maximum dose" refers hereinafter to the highest dose absorbed in a complete treatment (several directions) or in a single shot from a single direction in the case of a converging beam.

The term "maximum dose location" refers herein after to the location or locations where the maximum dose is received.

The term "target coverage index (TCI)" refers hereinafter to an index describing the exact coverage of the target volume in a treatment plan at a given prescription dose as expressed below:

$$TCI = \frac{PTV_{PD}}{PTV},$$

where PTV refers to the planned target volume (taking into account the machine limitation) and $PTV_{PD}$ refers to the prescribed dose target volume.

Reference is now made to FIG. 1, schematically illustrating a radiotherapy or radiosurgery treatment utilizing a converging x-ray beam source (100). The converging x-ray beam source (101) emits a converging x-ray beam (102). The beam is targeted towards a volume of treatment (VOT) (103) which is usually an organ infected with cancer within a patient's body (104). Before reaching the VOT the beam travels through other organs preceding the VOT (105). After exiting the VOT the beam travels through organs distal to the VOT (106). The converging x-ray beam source enables the VOT to receive a large dosage while the distal and preceding organs receive minimal dosage. Reducing the dosage to healthy tissue reduces the amount of side effects that the patient will suffer from. Therefore, using a converging beam source will reduce long term as well as short term side effects. The increased dose supplied to the VOT will increase the efficiency of the therapy and might even shorten the therapy course making it more tolerable to patients.

Figure 2:
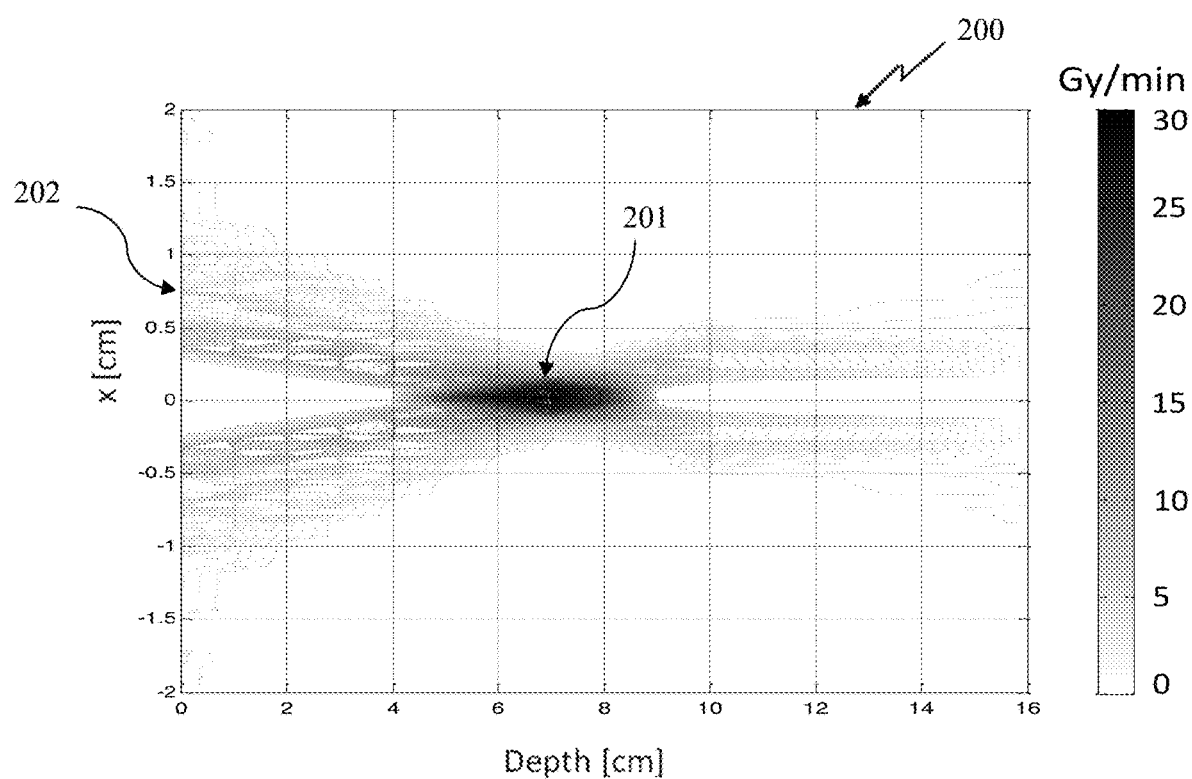
FIG. 2 is a 2-dimensional (2D) grey-scale dose distribution presentation of a longitudinal cross-section of the center of a single shot of a converging x-ray beam (200)

Reference is now made to FIG. 2, a 2-dimensional (2D) longitudinal cross-section of dose distribution presentation (200) of a single shot of a converging x-ray beam shown along a longitudinal cross-section at the center of the beam. The maximum dose at the tumor location (201) of over than 30 Gy/min is given at depth of 6-8 cm and with a transverse cross-section area of about 0.25 cm diameter at the center. The rest of the dose is diverged around this area and does not exceed about an average of 5 Gy/min. In this example the radiation penetrates the skin from the left (202). This shows that the beam can be concentrated in one specific area that is aimed at the volume of treatment (VOT) (201). The VOT is usually a cancerous tumor. The higher the dosage in this area the more successful the treatment is. The rest of the dose around is absorbed by healthy tissue and as result damages it. The lower the radiation is in these areas less adverse effects results from the treatment. The converging beam enable high dose to the VOT while relatively low doses to the area surrounding the VOT and therefore the treatment with this beam is more successful and causes les adverse effects.

Figure 3:
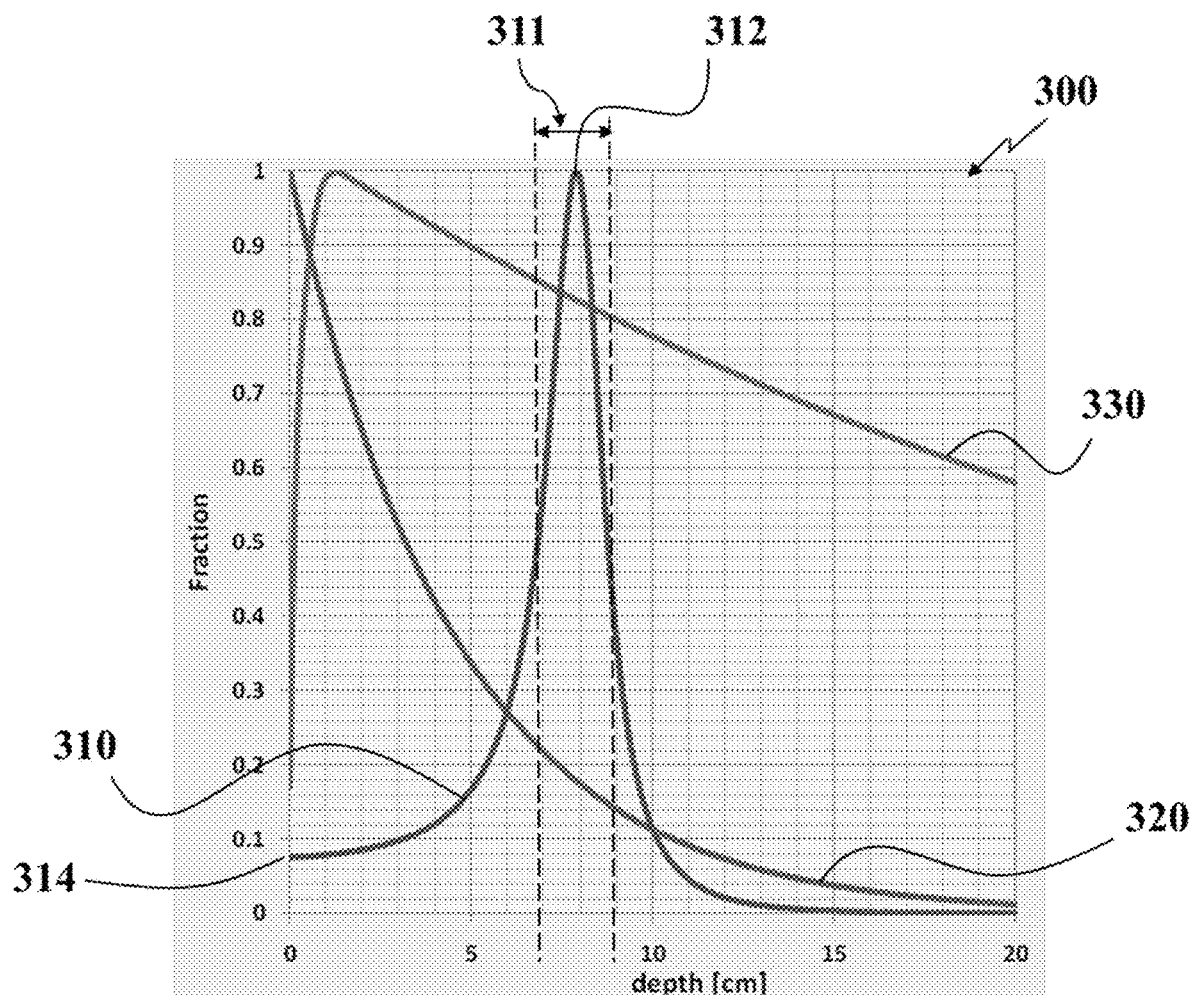
FIG. 3 is an illustration of the percentage of the dose distribution as function of depth of penetration of different types of x-ray beams.

Reference is now made to FIG. 3, an illustration of the percentage of the dose distribution as function of depth of penetration, which is called: Percentage Depth Dose (PDD) of different types of x-ray beams (300). The converging x-ray beam (310) distributes mainly in one region (311) resulting in very high dosage to a specific area while the surroundings of this areas receive much lower dosage. The two other beams, parallel beam from an orthovoltage X-ray source (320) and from a linear accelerator (330) distribute differently. They both smear on a very large area delivering high dosage close to the skin with no peak. When treating a cancerous tumor by radiotherapy or radiosurgery, it is very important that the beam will concentrate on a very specific volume while the surrounding volumes receive as little as possible of the beam. Therefore, the converging beam seems to be much more suitable for radiotherapy or radiosurgery treatments.

Figure 4:
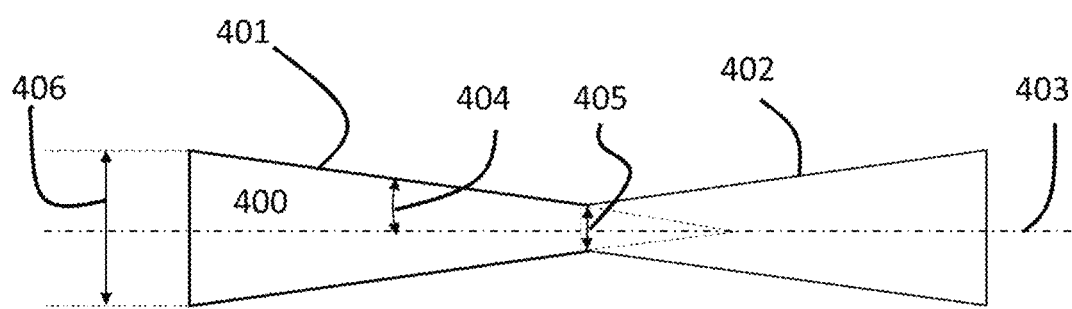

In order to achieve the described effects, one needs to define the parameters of a converging beams:

Reference is made now to FIG. 4 showing a longitudinal cross-sectional view (400) of a converging beam.

The purpose of the converging beam is to generate relatively large dosage at the target inside the body with as minimum as possible dosage at the entrance to the body at the skin. The ratio of the dose at the tumor to the dose at the entrance to the body, usually the skin, is defined:

A beam interacting with mater that has a cone shape can be written in general:

$$I(x) = I_0 \frac{1}{\text{cross-section at } x} e^{-\mu x}$$

where $I_0$ is the local intensity at the entrance and x is the depth. Regarding cross-section area. This depends on the cone type: If it's a full cone or a hollow cone with different wall thickness that can be variable, or few cones embedded inside each other.

If the cross-section is smaller, the radiation is spread into smaller area and the local dose is becoming higher. Thus, the dose as function of depth is becoming strong at the predetermined depth. To evaluate the alteration and improvement of the converging beam one would expect the dose at the target to the highest and the surrounding tissues to receive less dose, especially the dose at the entrance to the body to be as low as possible. In this patent we define the standards of how to evaluate the quality of a converging beam.

The converging property is a geometrical property, but it also depends on the material that it penetrates and the energy spectrum of the photons in use.

The easiest way and the direct way to evaluate the converging property is by direct valuation of the ratio of the dose at the target v.s. the dose at the entrance to the body. Other means of evaluations will be presented as well.

The converging definition and measurement should follow the following steps:

A standard depth in water will be 8 cm measurement in a water phantom. One places a converging beam emitting system, for example like one mentioned in U.S. Pat. No. 9,008,271 incorporated by reference in all its entirety. The distance of the lens is such that the focal waist of the beam is at depth 8 cm.

Obtaining the beam shape using means to measure the local dose, for example a moving small dosimeter in water in a water phantom. One should make multiple measurements at various places to obtain a full 3D isodose picture of the beam in the water, In general, a cone beam can be full or hollow with varying wall thickness or with several hollow cones embedded inside each other.

An option is shown in FIG. 3 for example where the dose is presented in a relative scale rather than absolute dose. In the example of FIG. 3 dose (312) of the converging beam (310) is presented as the fractional value normalized to 1 so the ratio at the entrance is the direct reading of the graph at the entrance (314), 0.08 in this example.

It is important to note that in some cases the entrance might be taken up to shallow depth of the order of 1 cm due to dose buildup of high energy photons like those from a LINAC. Thus, both other examples (320 & 330) in FIG. 3 cannot be considered converging.

In some cases it is convenient to use the ratio as the reciprocal of the skin dosage percentage:

$$Q_{me} \equiv \frac{1}{R_{em}} = \frac{\text{Maximum dose at the focus}}{\text{Dose at zero depth}}$$

This is convenient for some forms of treatment plans.

One can take a minimum requirement for a converging beam is $R_{em}$ to be maximum 0.7.

In the case of using the reciprocal form $Q_{me}$, it comes out as the minimum ratio of 1.4.

Additional way to evaluate the beam converging property is the beam longitudinal cross-section i.e. the envelope (401) prior to the focal target (405) to obtain the cone shape with a converging half angle (404).

The method to do that is for example by calculating the envelope converging angle using the obtained diameters:

$$\frac{D_e - D_w}{2L} = \tan \alpha \text{ or } \frac{0.25(R_{ew} - 1)}{L_{[mm]}} = \tan \alpha$$

Where $\alpha$ is the angle (404) in FIG. 4 and L is the depth. The predetermined depth 8 cm is in the scope of the present invention.

Additionally, one can use the above parameters to establish the important parameter of longitudinal focusing, or in other words how long is the strong dose rate region at the focal place in the direction of the beam propagation—the focal region longitudinal size.

Converging angle has a strong influence both on dose ratio at target v.s. zero depth and also on longitudinal focal size.

Another parameter is the beam divergence beyond the focal point.

All the above are used to design a treatment plan with maximum dose gradient at the tumor edges.

Reference is now made to FIG. 5 presenting a flowchart of method 500 of estimating dosimetric characteristics provided by an x-ray convergent irradiator. Method 500 starts with step 510 of providing said X-ray convergent irradiator comprising an X-ray source and a lens arrangement configured for forming an X-ray beam with a convergent envelope. The X-ray beam has an optical axis. Then, the X-ray irradiator is positioned above a water phantom such that a maximal dose location is located at a predetermined depth at step 520. Local doses in a plurality of points within said water phantom are measured at step 530. The data measured at the previous step form a 3D isodose map within the convergent envelope which propagates in the water phantom (step 540). The maximal measured dose within the convergent envelope is determined at step 550. Then, on the basis of obtained 3D isodose map, a cross-sectional diameter $D_w$ of a focal spot formed by the convergent envelope in a plane transversally oriented to the optical axis is determined at step 560. Similar to the previous step, a cross-sectional diameter $D_e$ at zero depth is determined at step 570. Then the following parameters are calculated: a percentage ratio of the maximal dose at zero depth to the maximal dose within said focal spot $$R_{em} \equiv \frac{\text{Dose at depth 0}}{\text{Maximum dose at the focus}}$$

(step 580) and a convergence angle given as arctan $$\alpha = \arctan\left(\frac{D_e - D_w}{2L}\right),$$

where $D_e$ and $D_w$ are cross-sectional diameters of the convergent envelope at the zero depth and the focal spot (step 590). Finally, a longitudinal size of said focal spot is determined according to a predetermined criterion at step 600.

The criterion of 80% is based on the treatment planning procedure issued by Commission on Radiation Units (ICRU) (see ICRU reports 50, 62, 83 and others regarding Gross Tumor Volume (GTV), Clinical Target Volume (CTV) and Planning Target Volume (PTV)).

The invention claimed is:

1. A method of irradiating a target by an X-ray convergent irradiator with an estimated dose; said method comprising steps of:
   a. estimating dosimetric characteristics provided by said X-ray convergent irradiator further comprising:
      i. providing said X-ray convergent irradiator; said irradiator comprising an X-ray source and a lens arrangement configured for forming an X-ray beam with a convergent envelope; said X-ray beam having an optical axis thereof;
      ii. positioning said X-ray irradiator above a water phantom such that a maximal dose location is located at a predetermined depth;
      iii. measuring local doses in a plurality of points within said water phantom;
      iv. obtaining a 3D isodose map of within said convergent envelope propagating in said water phantom;
      v. determining a maximal dose within said convergent envelope;
      vi. on a basis of said 3D isodose map, determining a cross-sectional diameter $D_w$ of a focal spot formed by said convergent envelope in a plane transversally oriented to said optical axis;
      vii. on a basis of said 3D isodose map, determining a cross-sectional diameter $D_e$ at zero depth in a plane transversally oriented to said optical axis;
      viii. calculating a percentage ratio of a maximal dose at zero depth to a maximal dose within said focal spot $$R_{em} = \frac{\text{Dose at zero depth}}{\text{Maximum dose at the focus spot}};$$

ix. calculating a convergence angle given as $$\arctan \alpha = \arctan\left(\frac{D_e - D_w}{2L}\right)$$

where $D_e$ and $D_w$ are cross-sectional diameters of said convergent envelope at said zero depth and said focal spot and L is a distance between said zero depth and focal spot; and
      x. determining a longitudinal size of said focal spot;
   b. on a basis of said obtained percentage ratio, convergence angle and longitudinal size of focal spot, estimating the dose to be provided to said target; and
   c. irradiating said target with said estimated dose.

2. The method according to claim 1, wherein said predetermined depth is 8 cm.

3. The method according to claim 1, wherein said predetermined criterion is a region where 80%-100% of said maximal dose is received.

4. The method of claim 1 wherein said water phantom is an equivalent of a human tissue.

5. A method of radio treatment a patient by an X-ray convergent irradiator using a treatment plan with prescribed dose; utilizing data measured by said method comprising steps of
   a. estimating dosimetric characteristics provided by said X-ray convergent irradiator further comprising:
      i. providing said X-ray convergent irradiator; said irradiator comprising an X-ray source and a lens arrangement configured for forming an X-ray beam with a convergent envelope; said X-ray beam having an optical axis thereof;
      ii. positioning said X-ray irradiator above a water phantom such that a maximal dose location is located at a predetermined depth;
      iii. measuring local doses in a plurality of points within said water phantom;
      iv. obtaining a 3D isodose map of within said convergent envelope propagating in said water phantom;
      v. determining a maximal dose within said convergent envelope;
      vi. on a basis of said 3D isodose map, determining a cross-sectional diameter $D_w$ of a focal spot formed by said convergent envelope in a plane transversally oriented to said optical axis;
      vii. on a basis of said 3D isodose map, determining a cross-sectional diameter $D_e$ at zero depth in a plane transversally oriented to said optical axis;
      viii. calculating a percentage ratio of a maximal dose at zero depth to a maximal dose within said focal spot $R_{em}$=Dose at zero depth/maximum dose at the focus spot;
      ix. calculating a convergence angle given as $\arctan \alpha = ((D_e - D_y)/2L)$ where $D_e$ and $D_w$ are cross-sectional diameters of said convergent envelope at said zero depth and said focal spot and L is a distance between said zero depth and focal spot; and
      x. determining a longitudinal size of said focal spot;
   b. on a basis of the obtained percentage ratio, convergence angle and longitudinal size of focal spot, estimating the dose to be provided to said patient;
   and
   c. irradiating said target with said estimated dose.

6. The method according to claim 5, wherein said predetermined depth is 8 cm.

7. The method according to claim 5, wherein said predetermined criterion is a region where 80%-100% of said maximal dose is received.

8. The methods of claims 5, wherein said water phantom is an equivalent of a human tissue.

\* \* \* \* \*